(12) United States Patent
Na et al.

(10) Patent No.: US 9,037,419 B2
(45) Date of Patent: May 19, 2015

(54) PORTABLE MATRIX PHASED ARRAY SPOT WELD INSPECTION SYSTEM

(71) Applicant: Edison Welding Institute, Columbus, OH (US)

(72) Inventors: Jeong K. Na, Centerville, OH (US); Sean T. Gleeson, Columbus, OH (US)

(73) Assignee: EDISON WELDING INSTITUTE, INC., Columbus, OH (US)

( * ) Notice: Subject to any disclaimer, the term of this patent is extended or adjusted under 35 U.S.C. 154(b) by 0 days.

(21) Appl. No.: 14/183,643

(22) Filed: Feb. 19, 2014

(65) Prior Publication Data

US 2014/0165730 A1 Jun. 19, 2014

Related U.S. Application Data

(63) Continuation-in-part of application No. 13/468,502, filed on May 10, 2012.

(60) Provisional application No. 61/484,312, filed on May 10, 2011.

(51) Int. Cl.
| | |
|---|---|
| *G01N 29/04* | (2006.01) |
| *G01N 29/06* | (2006.01) |
| *G01N 29/26* | (2006.01) |
| *G01N 29/28* | (2006.01) |

(52) U.S. Cl.
CPC .......... *G01N 29/043* (2013.01); *G01N 29/0645* (2013.01); *G01N 29/262* (2013.01); *G01N 29/28* (2013.01); *G01N 2291/106* (2013.01); *G01N 2291/2672* (2013.01)

(58) Field of Classification Search
None
See application file for complete search history.

(56) References Cited

U.S. PATENT DOCUMENTS

| | | | |
|---|---|---|---|
| 7,698,944 | B2 * | 4/2010 | Takada ........................... 73/588 |
| 7,926,349 | B2 | 4/2011 | Sargent |
| 7,984,651 | B2 | 7/2011 | Randall et al. |
| 8,076,824 | B2 | 12/2011 | Sawada et al. |
| 8,079,263 | B2 | 12/2011 | Randall et al. |
| 8,164,982 | B2 | 4/2012 | Okuda et al. |
| 8,166,822 | B1 | 5/2012 | Urbano et al. |
| 8,220,334 | B2 | 7/2012 | Klessel et al. |
| 8,365,584 | B1 | 2/2013 | Quinones et al. |
| 8,485,036 | B2 | 7/2013 | Crumpton et al. |

(Continued)

FOREIGN PATENT DOCUMENTS

| | | |
|---|---|---|
| WO | 2012058473 A1 | 5/2012 |
| WO | 2012103628 A1 | 8/2012 |

(Continued)

*Primary Examiner* — Aditya Bhat
(74) *Attorney, Agent, or Firm* — McNees, Wallace & Nurick, LLC

(57) ABSTRACT

A portable system for non-destructively characterizing spot welds that includes at least one matrix phased array probe and a body, wherein the body is designed to be hand-held and further includes an ergonomically designed outer casing; at least one input for connecting to the at least one matrix phased array probe; ultrasonic phased array transmitting and receiving circuitry in electrical communication with the at least one input; a touch screen computer that further includes at least one data processor running software that includes at least one imaging algorithm for processing data received from the probe and generating color coded ultrasonic C-scan images of characterized welds; and at least one monitor for displaying the color coded ultrasonic C-scan images of the characterized welds in real time.

20 Claims, 10 Drawing Sheets

(56) References Cited

U.S. PATENT DOCUMENTS

| | | |
|---|---|---|
| 8,499,634 B2 | 8/2013 | Urbano et al. |
| 8,499,635 B2 | 8/2013 | Klessel et al. |
| 8,521,446 B2 | 8/2013 | Zhang et al. |
| 8,544,714 B1 | 10/2013 | Obaditch et al. |
| 8,554,328 B2 | 10/2013 | Faraji et al. |
| 8,600,299 B2 | 12/2013 | Randall et al. |
| 8,616,062 B2 | 12/2013 | Kono et al. |
| 8,649,185 B2 | 2/2014 | Wodnicki et al. |
| 8,656,783 B2 | 2/2014 | Randall et al. |
| 8,689,850 B2 | 4/2014 | Hull |
| 8,695,429 B2 | 4/2014 | Urbano et al. |
| 8,746,070 B2 | 6/2014 | Tippit, Jr. et al. |
| 2010/0286527 A1 | 11/2010 | Cannon et al. |
| 2011/0120223 A1 | 5/2011 | MacLauchlan et al. |
| 2012/0034044 A1 | 2/2012 | Sloan |
| 2012/0065937 A1 | 3/2012 | de Graff et al. |
| 2012/0091185 A1 | 4/2012 | Ume et al. |
| 2012/0167690 A1 | 7/2012 | Yamano |
| 2012/0243771 A1 | 9/2012 | Matsumoto et al. |
| 2012/0272739 A1 | 11/2012 | Both et al. |
| 2013/0167646 A1 | 7/2013 | Frederick et al. |
| 2013/0181574 A1 | 7/2013 | Chaggares et al. |
| 2013/0194891 A1 | 8/2013 | Kristoffersen et al. |
| 2013/0228560 A1 | 9/2013 | Ume et al. |
| 2013/0255384 A1 | 10/2013 | Putsherry et al. |
| 2013/0308419 A1 | 11/2013 | Singh et al. |
| 2013/0312528 A1 | 11/2013 | Feydo |
| 2013/0315035 A1 | 11/2013 | Tai |
| 2013/0319120 A1 | 12/2013 | Fetzer et al. |
| 2013/0338941 A1 | 12/2013 | Lin et al. |
| 2014/0107534 A1 | 4/2014 | Du et al. |

FOREIGN PATENT DOCUMENTS

| | | |
|---|---|---|
| WO | 2012167380 A1 | 12/2012 |
| WO | 2013044350 A1 | 4/2013 |
| WO | 2014062467 A1 | 4/2014 |
| WO | 2014081721 A1 | 5/2014 |
| WO | 2014100217 A1 | 6/2014 |

* cited by examiner

3-Dimensional Array Element

- Red Elements: 0 delay
- Blue Elements: (n) nano-second delay
- Green Element: (n+m) nano-second delay continues till 8th group

PORTABLE MATRIX PHASED ARRAY SPOT WELD INSPECTION SYSTEM

CROSS-REFERENCE TO RELATED APPLICATIONS

This patent application is a continuation-in-part of U.S. patent application Ser. No. 13/468,502 filed on May 10, 2012 and entitled "3-D Matrix Phased Array Spot Weld Inspection System", which claimed the benefit of U.S. Provisional Patent Application Ser. No. 61/484,312 filed on May 10, 2011 and entitled "Three-Dimensional Matrix Phased Array Spot Weld Inspection System", the disclosures of which are incorporated by reference herein in their entirety and made part of the present U.S. utility patent application for all purposes.

BACKGROUND OF THE INVENTION

The present invention relates generally to inspection systems for use in assessing the performance of industrial manufacturing processes, and more specifically to a nondestructive inspection system for assessing the quality of resistance spot welds and other weld joints.

Sheet metal joining processes are widely used in many industries including the aerospace and automotive industries. Among these processes, resistance spot welding is a very common procedure used to join metal sheets because it has high process speed and is easily adopted in mass production lines. Seam welding, weld bonding, adhesive joining, soldering, and brazing have also gained acceptance. The quality control of such joining processes has been recognized as an important issue to manufacturers. The quality of weld joints is affected by the joining process itself and by the design of the joint. Many factors are considered, including metallurgic reactions, thermal behaviors, chemical composition, starting condition of the base metal, welding and bonding conditions, and the welding and bonding equipment used during the process. Furthermore, the intricate relationship between these factors makes it difficult to control the quality of the weld joint and difficult to inspect the weld joint in a nondestructive manner.

Acoustic methods are commonly used nondestructive testing methods for various inspection applications. Unlike other nondestructive testing methods, acoustic methods provide both surface and internal information. Moreover, acoustic methods allow for deeper penetration into specimens and higher sensitivity to small discontinuities in a weld joint. Acoustic methods, however, do have limitations. The most significant limitations include the requirement of a skillful operator for using the testing device and analyzing acoustic data, as well as the very subjective nature of identifying a stuck or cold weld or inadequate bond, such as a kissing bond. Accordingly, the field of ultrasonic nondestructive evaluation (NDE) is in need of a reliable process or technique for identifying poor quality joints in a manner that eliminates the involvement of a skilled operator and the subjective interpretation of test data.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first portable system for non-destructively characterizing a spot weld is provided. This system includes at least one matrix phased array probe and a body. The matrix phased array probe further includes a plurality of ultrasonic transducer elements arranged in a curved array at one end of the probe that are operative to both generate ultrasonic signals and to receive reflections thereof; and a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array. The body is designed to be handheld and further includes an ergonomically designed outer casing; at least one input for connecting to the at least one matrix phased array probe; ultrasonic phased array transmitting and receiving circuitry in electrical communication with the at least one input; a touch screen computer that further includes at least one data processor running software that includes at least one imaging algorithm for processing data received from the probe and generating color coded ultrasonic C-scan images of characterized welds; and at least one monitor for displaying the color coded ultrasonic C-scan images of the characterized welds in real time.

In accordance with another aspect of the present invention, a second portable system for non-destructively characterizing a spot weld is provided. This system also includes at least one matrix phased array probe and a body. The matrix phased array probe further includes a plurality of ultrasonic transducer elements arranged in a curved array at one end of the probe that are operative to both generate ultrasonic signals and to receive reflections thereof; and a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array. The body is designed to be handheld and further includes an ergonomically designed outer casing having a handle that has been adapted to store the matrix phased array probe; at least one input for connecting to the probe; ultrasonic phased array transmitting and receiving circuitry in electrical communication with the at least one input; a touch screen computer that further includes at least one data processor running software that includes at least one imaging algorithm for processing data received from the probe and generating color coded ultrasonic C-scan images of characterized welds; at least one monitor for displaying the color coded ultrasonic C-scan images of the characterized welds in real time; and at least one rechargeable battery.

In yet another aspect of this invention, a third portable system for non-destructively characterizing a spot weld is provided. This system also includes at least one matrix phased array probe and a body. The matrix phased array probe further includes a plurality of ultrasonic transducer elements arranged in a curved array at one end of the probe, wherein the transducer elements are further arranged into discrete subgroups, wherein each subgroup may be activated independently of the other subgroups and at different time intervals; and wherein the transducer elements are operative to both generate ultrasonic signals and to receive reflections thereof; and a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array. The body is designed to be hand-held and further includes an ergonomically designed outer casing having a handle that has been adapted to store the matrix phased array probe, and at least one arm rest for supporting the body; at least one input for connecting to the probe; ultrasonic phased array transmitting and receiving circuitry in electrical communication with the at least one input; a touch screen computer, wherein the touch screen computer further includes at least one data processor running software that includes at least one imaging algorithm for processing data received from the probe and generating color coded ultrasonic C-scan images of characterized welds, and wherein C-scan images further include average diameter of weld nugget and fused area for each characterized weld; at least one monitor for displaying the color coded ultrasonic C-scan images of the characterized welds in real time; and at least one rechargeable battery.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Figure 1:
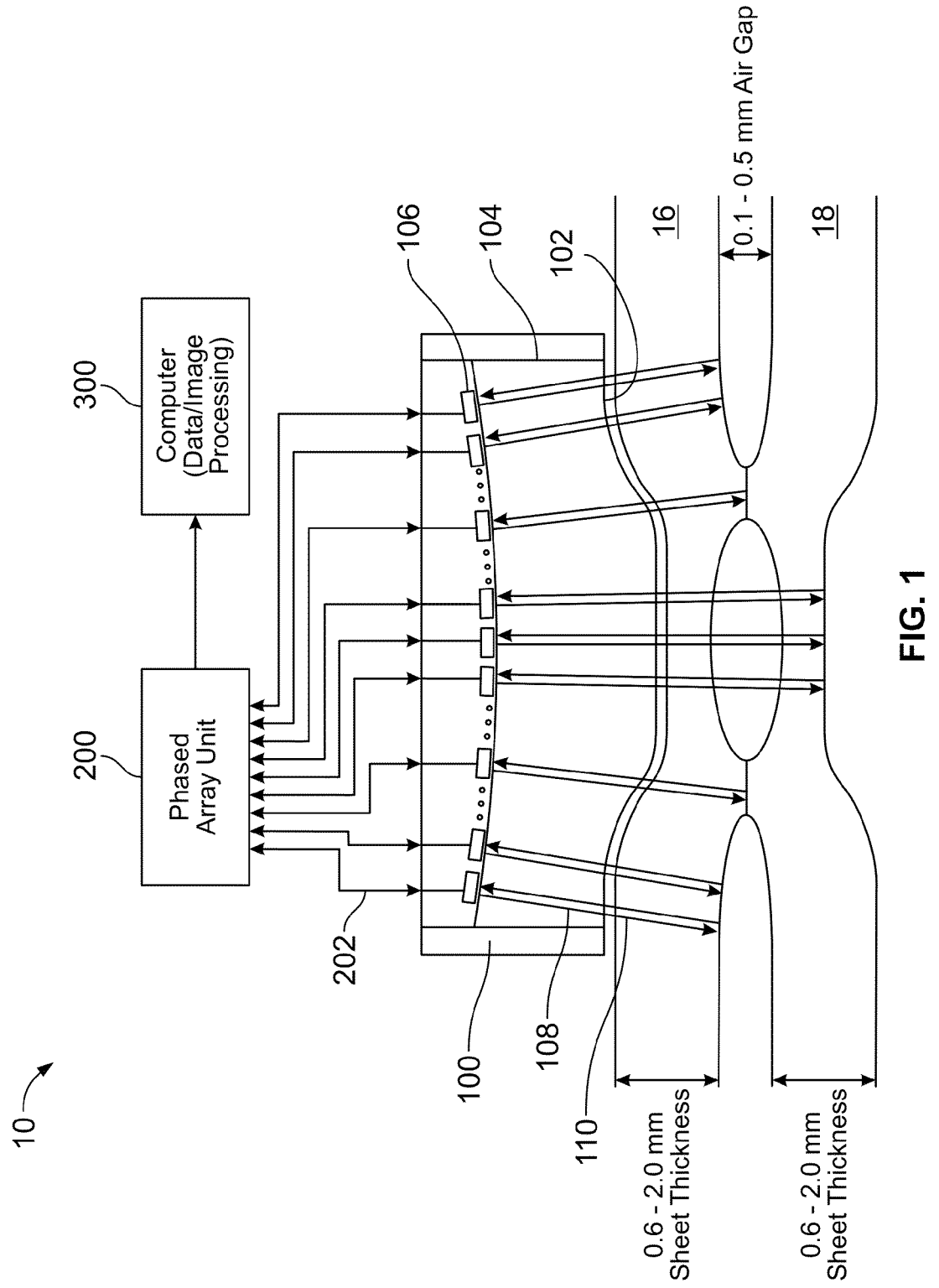
FIG. 1 is a block diagram showing the primary components of a three-dimensional matrix phased array spot weld inspection system in accordance with an exemplary embodiment of the present invention.

Exemplary embodiments of the present invention are now described with reference to the Figures. Reference numerals are used throughout the detailed description to refer to the various elements and structures. In other instances, well-known structures and devices are shown in block diagram form for purposes of simplifying the description. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present application incorporates by reference herein U.S. patent application Ser. No. 12/186,047, in its entirety for all purposes. With regard to the nomenclature used herein, the present invention is described as being useful for analyzing the integrity of a resistance spot weld between a first and second workpiece or upper and lower sheets of metal. However, this invention is applicable to all welds regardless of material, configuration, or the number of workpieces, as well as adhesive bonds. Thus, while the present disclosure generally refers to a stuck weld, one skilled in the art will appreciate that the present invention detects stuck portions of joints, which are often referred to as kissing bonds or weak bonds in the field of adhesives. This invention is also applicable to metals and nonmetals alike and is not limited to fusion welding, but may also be used to examine solid state welds, brazed and soldered joints. Thus, while this method has particular application in the automated analysis of spot welds, it may also be used to evaluate continuous bonds.

A stuck weld or stuck joint occurs when workpieces (e.g., pieces of sheet metal) are held together by localized fusion at the welding interface, but no weld button or weld nugget has formed as a result of the welding process. A stuck weld typically results from heat at the welding interface being insufficient to create nugget growth. In the absence of a properly formed weld nugget, fusion may occur at certain points of contact between the sheets of metal. With coated materials, coatings can melt and refreeze, effectively soldering the parts together. The resulting bonds are often strong enough to hold the workpieces together under light loads, but reasonable force will pull them apart. If ultrasonic testing is used to analyze weld integrity, transmitted ultrasonic beams (i.e., sound waves) will not pass through the interface between sheets if no fusion has occurred. If a stuck weld as occurred, resulting in fusion, but no weld nugget, transmitted ultrasonic beams will pass partially though the sheet interface. If a weld nugget has been properly formed, transmitted ultrasonic beams will pass completely through the sheet interface.

Phased Array Ultrasonic Testing (PAUT) may be used for flaw detection, sizing, and imaging. PAUT technology is the ability to modify electronically the acoustic probe characteristics. Probe modifications are performed by introducing time shifts in the signals sent to (pulse) and received from (echo) individual elements of an array probe. Three common formats for collecting and displaying ultrasonic data for purposes of non-destructive evaluation are A-scan, B-scan and C-scan presentations. Each presentation mode provides a means for visualizing and evaluating the region of material being inspected. An A-scan is a simple RF waveform presentation showing the time and amplitude of an ultrasonic signal, as commonly provided by conventional ultrasonic flaw detectors and waveform display thickness gages. A-scan is an amplitude modulation scan, and as generally applied to pulse echo ultrasonics, horizontal and vertical sweeps are proportional to time or distance and amplitude or magnitude respectively. Thus the location and magnitude of acoustical interface are indicated as to depth below the transducer. The relative amount of energy received is plotted along the vertical axis and the elapsed time (which may be related to the sound energy travel time within the material) is displayed along the horizontal axis. Most instruments utilizing an A-scan display allow the signal to be displayed in its natural radio frequency form (RF) as a fully rectified RF signal or as either the positive or negative half of the RF signal. In the A-scan presentation, relative discontinuity size can be estimated by comparing the signal amplitude obtained from an unknown reflector to that from a known reflector. Reflector depth can be determined by the position of the signal on the horizontal sweep. A C-scan from a phased array system involves an ultrasonic probe being physically moved along one axis while the beam electronically scans along the other axis according to the focal law sequence. Signal amplitude or depth data is collected within gated regions of interest. Data is plotted with each focal law progression, using the programmed beam aperture. Utilizing a matrix phased array probe, beam steering can be accomplished in multiple directions.

With reference to the Figures, an exemplary embodiment of the present invention provides a nondestructive inspection system for assessing the quality of resistance spot welds. As shown in FIG. 1, which is a block diagram of an exemplary embodiment, spot weld inspection system 10, is operative to assess the quality of weld 12, which is formed at interface 14, which is located between upper sheet 16 and lower sheet 18 (both having a sheet thickness of about 0.6 mm to about 2.0 mm). An air gap of about 0.1 mm to about 0.5 mm may be present between upper sheet 16 and lower sheet 18. A three-dimensional, matrix phased array probe 100 is placed on the region of upper sheet 16 that is located over the welded area. A curved array of ultrasonic elements 106 is used to transmit a plurality of ultrasonic beams 108 into the welded area and to capture the associated reflections 110 of those ultrasonic beams. Phased array unit 200 is in electrical communication with the plurality of ultrasonic elements 102 through a plurality of signal pathways 202. Phased array unit 200 is also in electrical communication with computer 300, which processes incoming ultrasonic data and generates a visual representation of the welded area. Probe 100 includes flexible membrane 102, which allows the tip of the probe to conform to the contour of the welded area and fluid filled chamber 104 or solid sound delay material for focusing and steering ultrasonic beams 108. Because flexible membrane 102 is capable of conforming to curved surfaces as shown in FIG. 1, and because the array of transducer elements 106 is configured in a curved geometry (see FIG. 1), the matrix phased array system of this invention is referred to as "three-dimensional" as opposed a "two-dimensional" system which uses a probe having a flattened array and a flat tip.

Figure 2A:
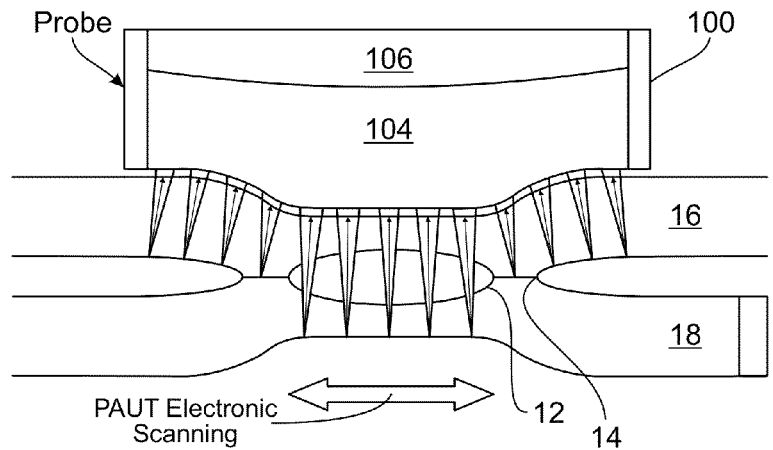
FIGS. 2a-c provide illustrations of test results derived from analyzing a good spot weld using the system of FIG. 1.
Figure 2B:
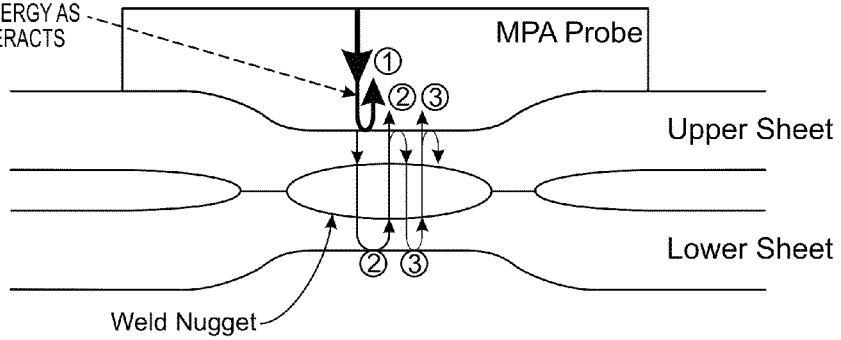
Figure 2C:
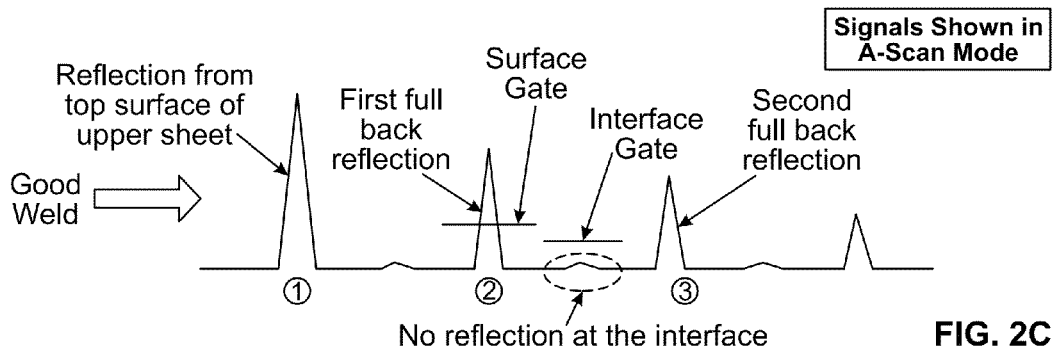
Figure 3:
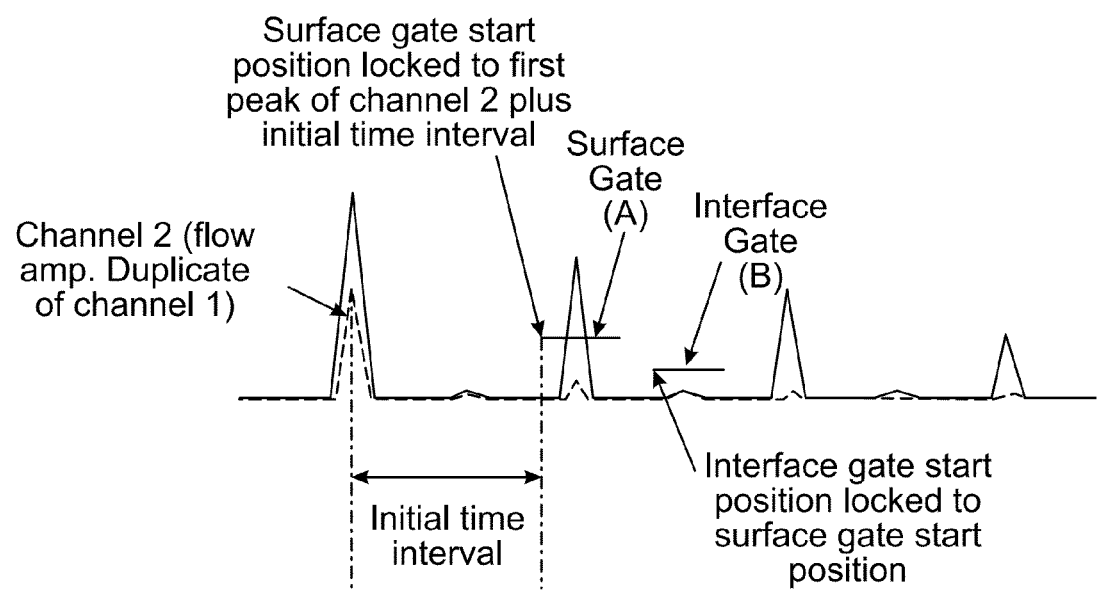
FIG. 3 provides a visual representation in A-scan mode of the electronic gates included in the weld inspection system of FIG. 1.

FIGS. 2a-c provide illustrations of test results derived from analyzing a good spot weld using system 10. In FIG. 2a, ultrasonic beams travel completely through weld 12 and interface 14 and reflect back to probe 100 from the backside of lower sheet 18. FIG. 2b illustrates diagrammatically the direction and relative strength of each sound wave as it transmits and reflects at interface 14. In FIG. 2b, a thinner line represents loss of acoustic energy as the sound wave interacts with interface 14. The reflected signals designated as circled 1, 2, and 3 correspond to the peaks shown in the A-scan presented in FIG. 2c. FIG. 2c provides the signals derived from testing in A-scan mode, wherein signal 1 represents the reflection from the top surface of upper sheet 16, signal 2 represents the first full back reflection, and signal 3 represents the second full back reflection. The horizontal line drawn through signal 2 represents a surface gate and the horizontal line adjacent to signal 2 represents an interface gate (see discussion below.)

Based on the ultrasonic energy transmission and reflection at weld interface 14 and the back side of lower sheet 18, system 10 uses two adjustable electronic gates to filter out all unwanted reflected signals. The two signals that pass through the gates are either the reflected signal from the back side of the second sheet of metal or the reflected signal from the interface of the two sheet metals. The first gate is called the "surface gate" and the second gate is called the "interface gate". This approach differs from the current commercially available systems that utilize an attenuation coefficient compensation method. In such systems, multiple reflections from all of surfaces and the interface are taken into account to determine attenuation coefficients and make a correction for acoustic energy loss caused by the spot weld fusion, assuming that the microstructure of fused section of the spot weld has a higher attenuation coefficient compared to a stuck weld condition. As disclosed and claimed in U.S. patent application Ser. No. 12/186,047, which is incorporated by reference herein, each ultrasonic element in array 106 generates a primary ultrasonic beam and a secondary ultrasonic beam wherein the primary ultrasonic beam is high gain and wherein the secondary ultrasonic beam is low gain; and wherein the primary and secondary ultrasonic beams are fired in within very close proximity to one another (i.e., milliseconds). As shown in FIG. 4, channel 2 is a low amplitude duplicate of channel 1 in each peak. The initial time interval shown is measured from the center of the first peak to the surface gate start position. The surface gate start position is locked to the first peak of channel 2 plus the initial time interval. The interface gate start position is locked to the surface gate start position. System 10 measures the ration of signal amplitude (height) between gate A and B and only signals between the gate start and end positions are considered.

Figure 4A:
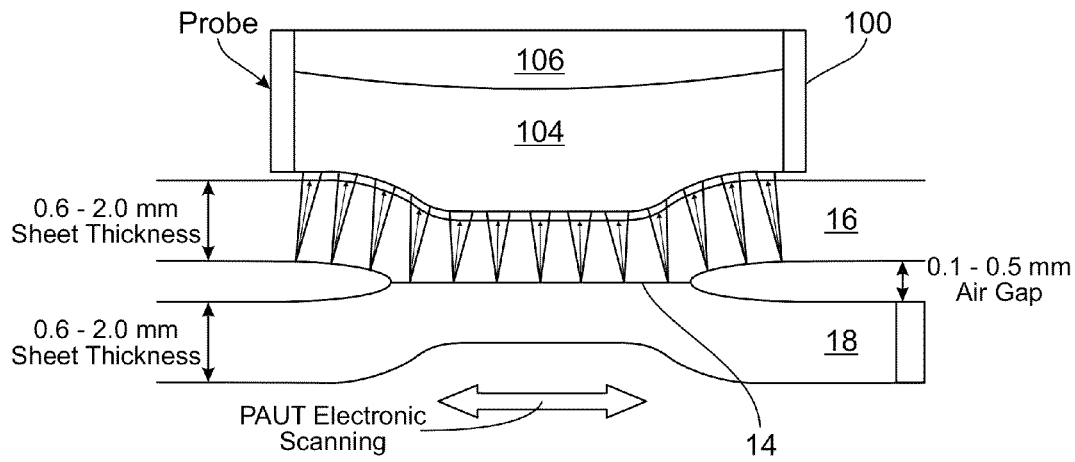
FIGS. 4a-c provide illustrations of test results derived from analyzing a poor spot weld using the system of FIG. 1.
Figure 4B:
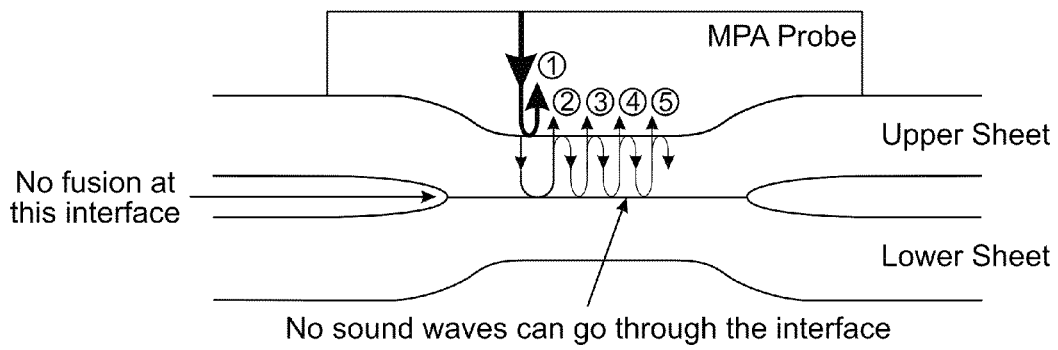
Figure 4C:
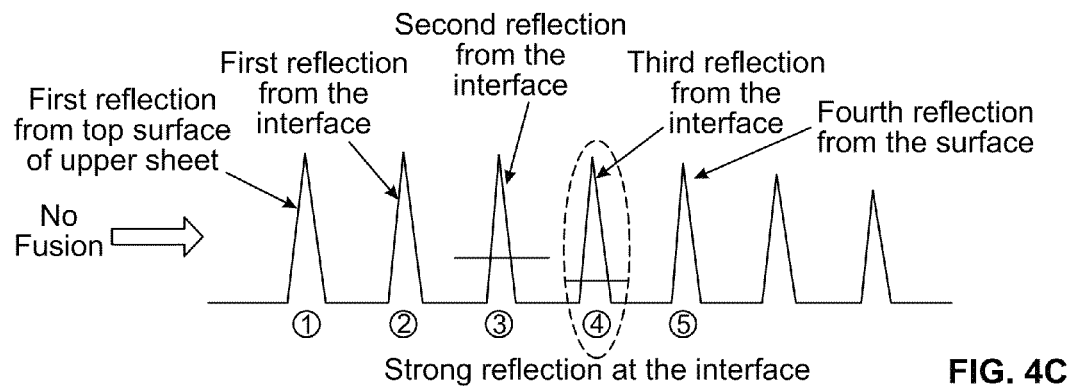

FIGS. 4a-c provide illustrations of test results derived from analyzing a poor spot weld using system 10. In FIG. 4a, because no weld nugget exists, ultrasonic beams do not travel completely through interface 14, but rather reflect back to probe 100 from interface 14. FIG. 4b illustrates diagrammatically the direction and relative strength of each sound wave as it reflects at interface 14. In FIG. 4b, a thinner line represents loss of acoustic energy as the sound wave interacts with interface 14. The reflected signals designated as circled 1, 2, 3, 4, and 5 correspond to the peaks shown in the A-scan presented in FIG. 4c. FIG. 4c provides the signals derived from testing in A-scan mode, wherein signal 1 represents the first reflection from the top surface of upper sheet 16, signal 2 represents the first reflection from interface 14, signal 3 represents the second reflection from interface 14, signal 4 represents the third reflection from interface 14, and signal 5 represents the fourth reflection from interface 14. The horizontal line drawn through signal 3 represents the surface gate and the horizontal line drawn though signal 4 represents the interface gate (see discussion above.)

Figure 5A:
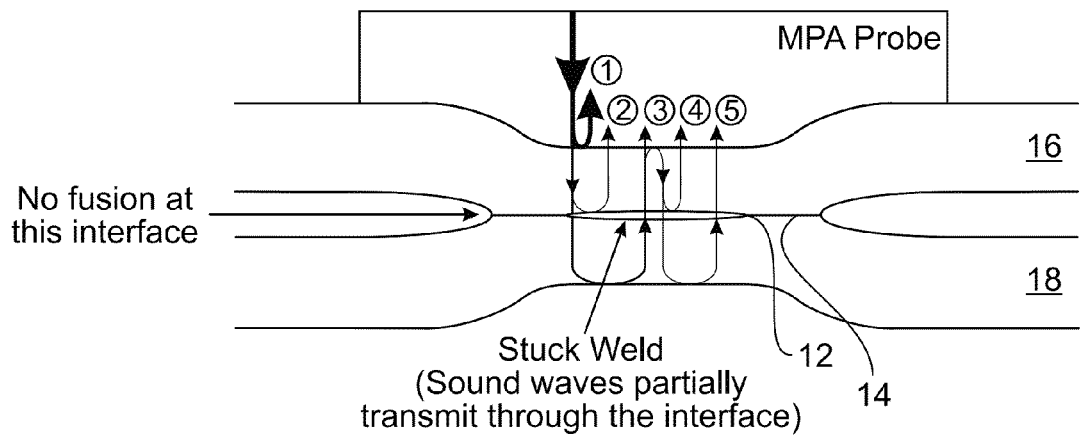
FIGS. 5a-b provide illustrations of test results derived from analyzing a stuck weld using the system of FIG. 1.
Figure 5B:
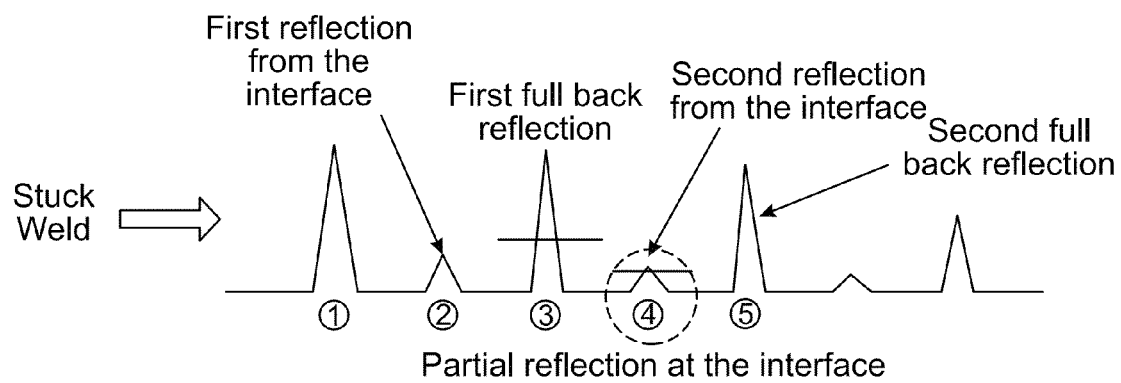

FIGS. 5a-b provide illustrations of test results derived from analyzing a stuck weld using system 10. Because an incomplete or poorly formed weld exists, ultrasonic beams travel only partially through interface 14, while intermediate echoes appear between the echoes of interface 14 and full back wall reflection. FIG. 5a illustrates diagrammatically the direction and relative strength of each sound wave as it transmits and reflects at interface 14. In FIG. 5a, a thinner line represents loss of acoustic energy as the sound wave interacts with interface 14. The reflected signals designated as circled 1, 2, 3, 4, and 5 correspond to the peaks shown in the A-scan presented in FIG. 5b. FIG. 5b provides the signals derived from testing in A-scan mode, wherein signal 2 represents the first reflection from interface 14, signal 3 represents the first full back reflection, signal 4 represents the second reflection from interface 14, and signal 5 represents the second full back reflection. The horizontal line drawn through signal 3 represents the surface gate and the horizontal line drawn though signal 4 represents the interface gate (see discussion above.)

Figure 6A:
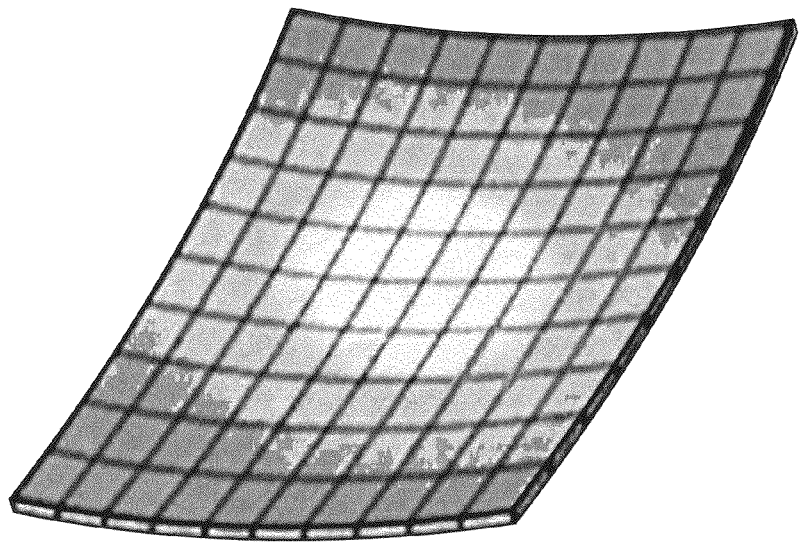
FIGS. 6a-b illustrate the shape of the 3-D curved probe element as well as various firing sequences for the sub-element groups.
Figure 6B:
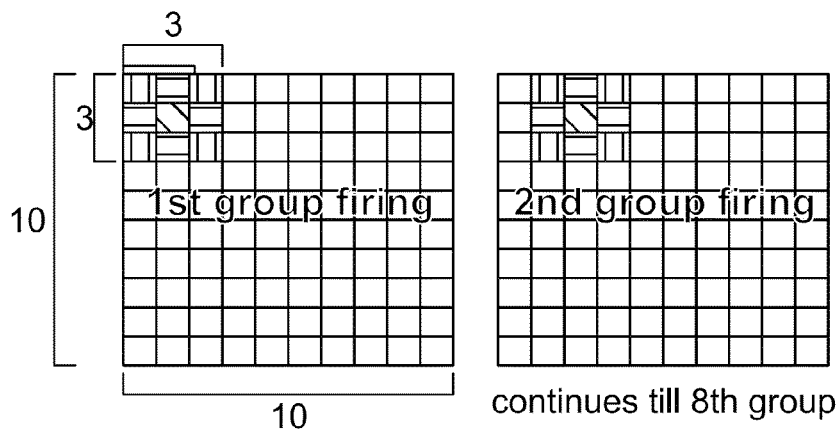
Figure 6B:
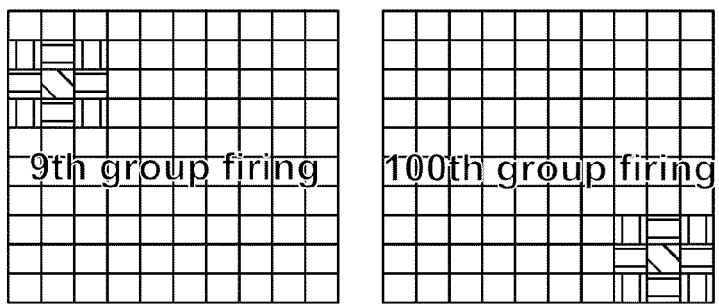

FIGS. 6a-b illustrate the geometry of the curved three-dimensional probe element (FIG. 6a) as well as various firing sequences for the sub-element groups (FIG. 6b). Acoustic probe 100 includes a plurality of ultrasonic transducer elements 106 arranged in a three-dimensional array and having a combination of materials for allowing the probe to conform to the contoured surface of a spot weld while enabling the sound energy to be transferred directly into the spot weld under test. An excitation element (phased array unit 200) is coupled to the array and a subset group of transducer elements are combined to send an ultrasonic beam toward a spot weld. Each transducer element in a subset group may be pulsed at different time intervals (phase delay) and their individual waves summed to produce a focusing effect of the beam as well as a steering effect. Other three-dimensional arrangements are possible for optimizing the performance for specific applications. The total number of elements, overall dimension, and operating frequency determine the overall three-dimensional surface contour shape and its operating characteristics and parameters.

Figure 7A:
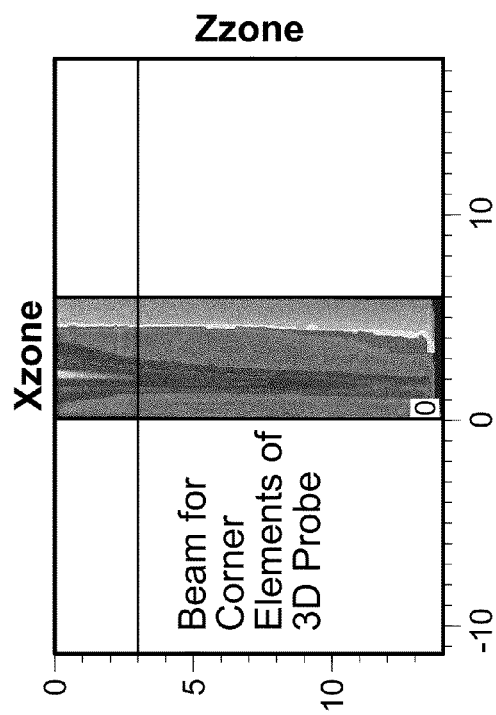
FIGS. 7a-d provide modeling verification of the benefits of a 3-D curved probe design versus a 2-D flat probe design.
Figure 7B:
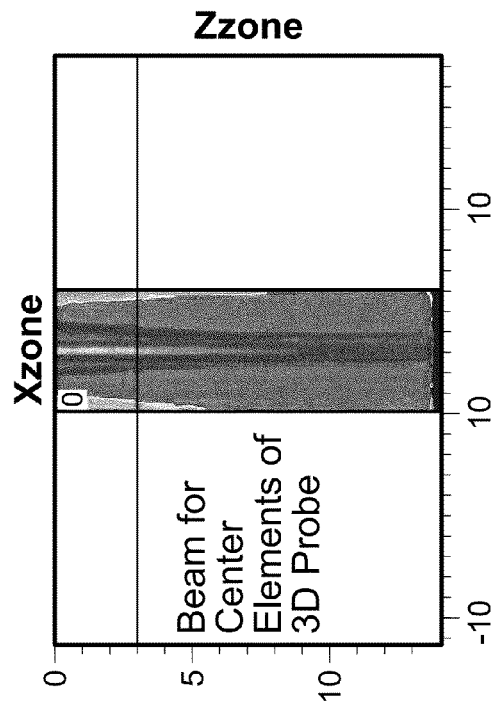
Figure 7C:
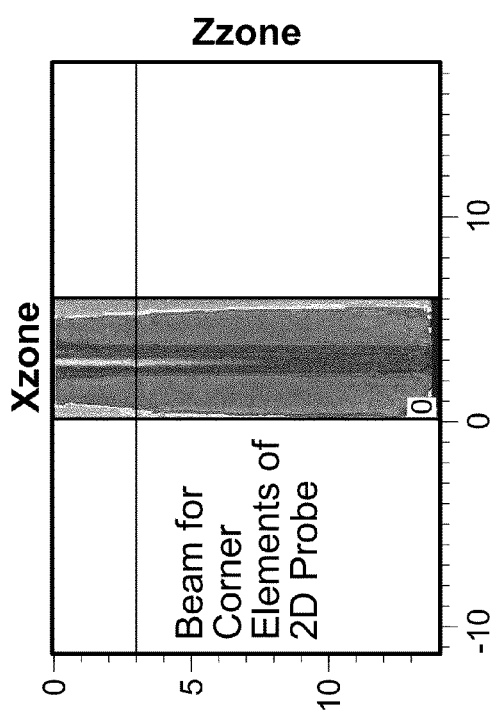
Figure 7D:
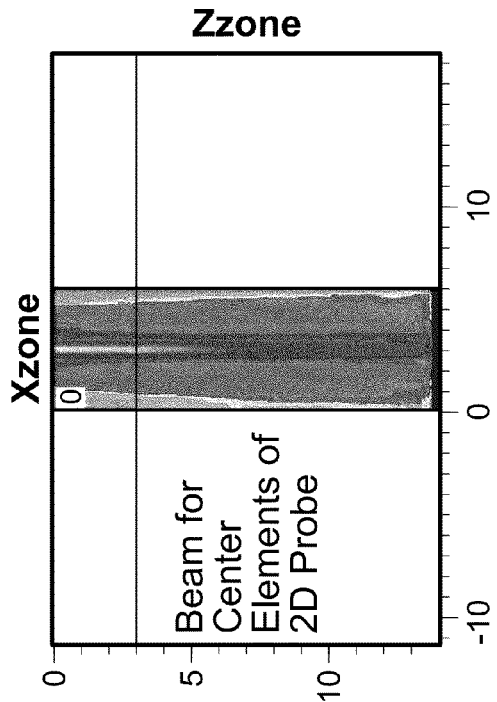

The design of the three-dimensional probe permits inspection of a larger physical area with a smaller probe, thereby allowing for improved probe access as well as a wider coverage area compared to two-dimensional designs. The three-dimensional geometrical arrangement provides optimized accuracy and sensitivity in particular regions of the weld joint. As illustrated by FIGS. 7a-d, the result of corner elements of the three-dimensional curved probe shown in FIG. 7a illustrates that the beam launch angle is more steered to the normal direction of the typical spot weld indentation when compared to the two-dimensional flat probe case shown in FIG. 7c. There is no noticeable change in the beam quality for the center elements for both three-dimensional (FIG. 7b) and two-dimensional (FIG. 7d) probes. Without losing the high fidelity of inspection capability with the two-dimensional matrix phased array probe, the three-dimensional probe extends the coverage area from the built-in curvature of the probe itself. This invention therefore allows inspection of a larger weld area with a smaller probe diameter, allowing improved access. It may also allow use of fewer numbers of elements, reducing overall system cost, while still covering the entire weld area.

Figure 8:
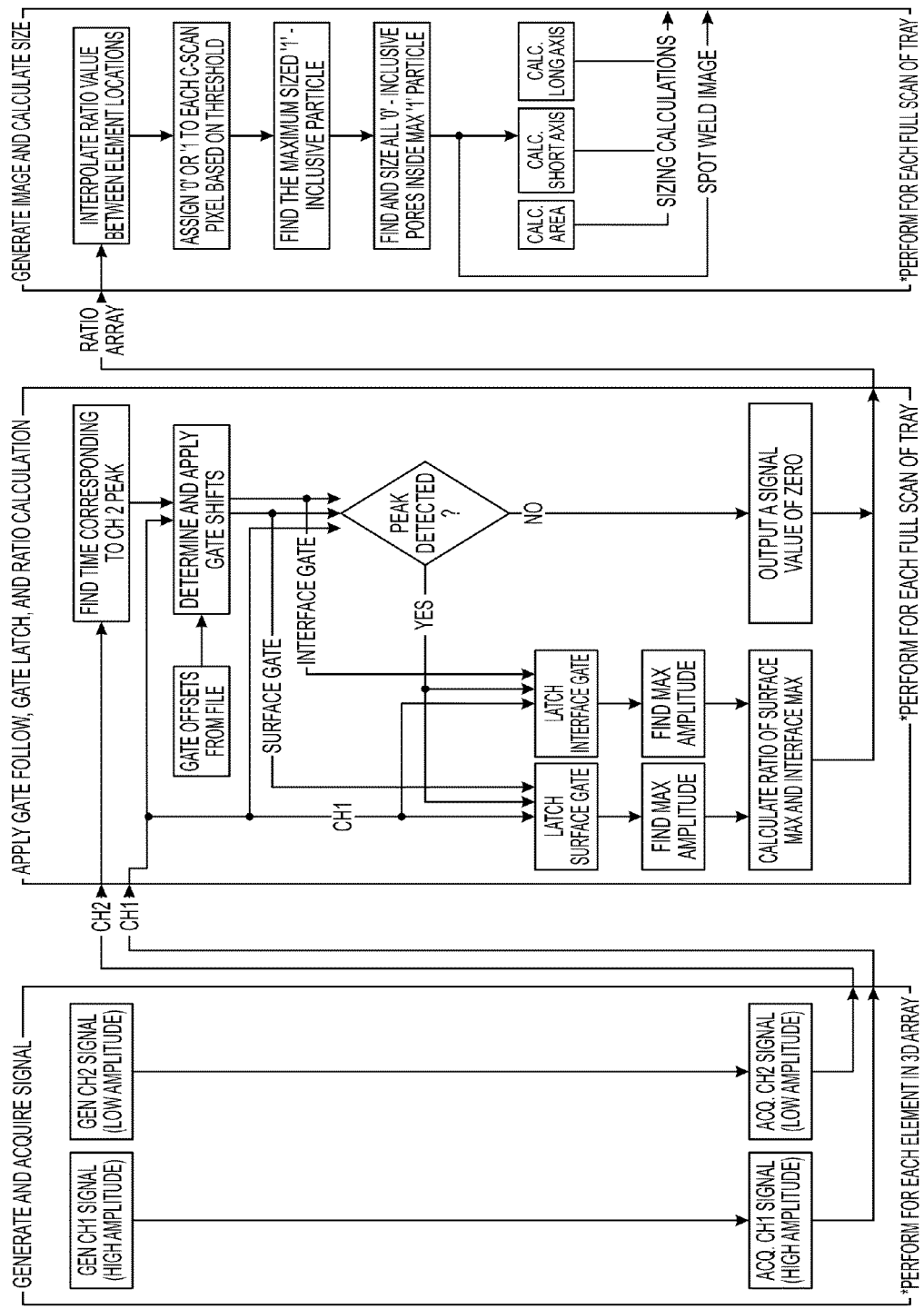
FIG. 8 provides a data flow chart for an exemplary embodiment of the spot weld inspection process of the present invention.
Figure 9:
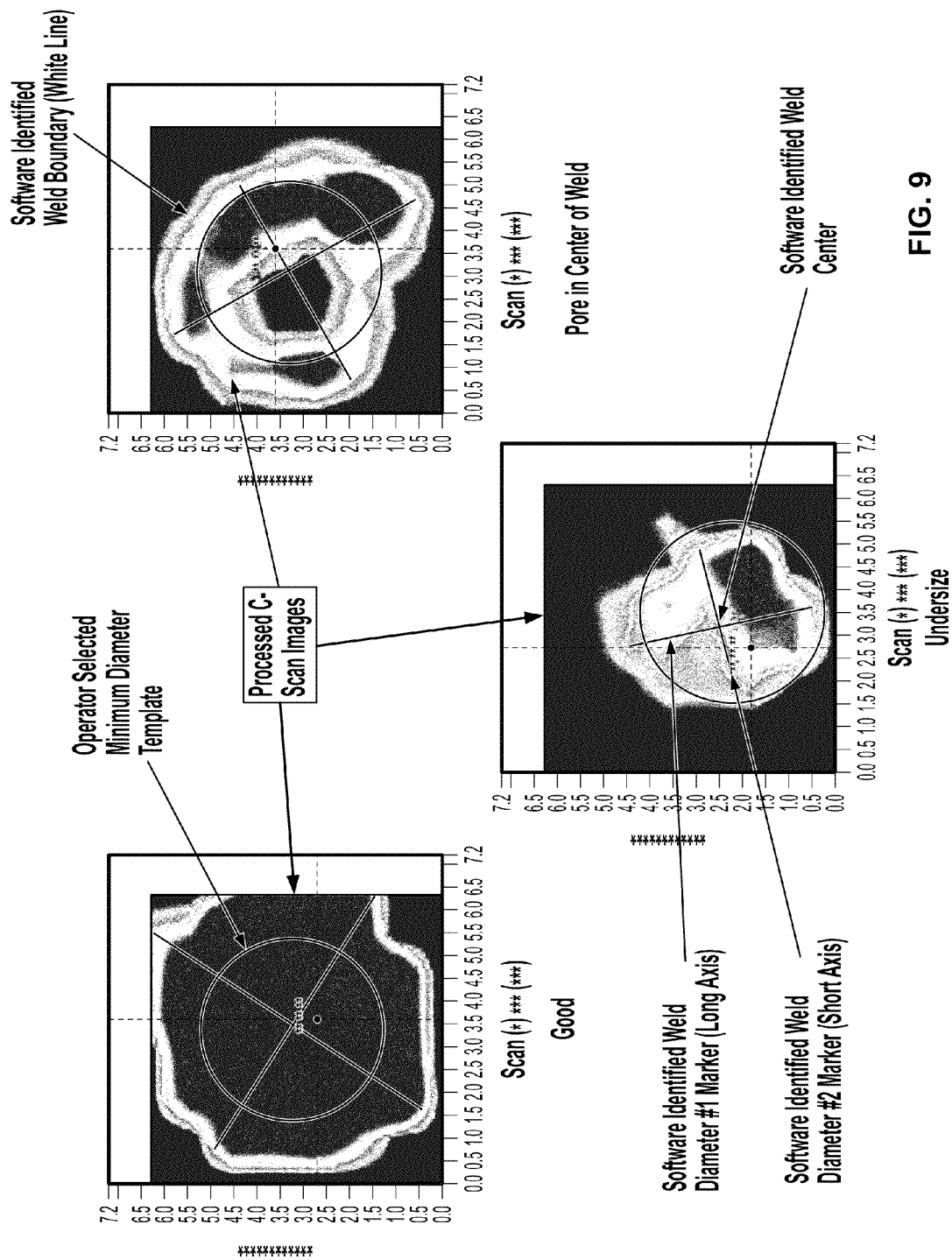
FIG. 9 provides examples of imaging results for various spot weld conditions.

In various embodiments of this invention, a computerized controller is coupled to acoustic probe 100 and transducer elements 106 for directing transmission of the ultrasonic signals and for summing and receiving responses therefrom. With general reference to FIG. 8 (which provides a flowchart that illustrates the function of one possible operating system), the controller is operative to (i) generate and acquire acoustic signals; (ii) detect the surface of the spot weld for each element grouping; (iii) adjust instrument gating to compensate for surface profile and differences in probe orientation; (iv) measure the signal amplitude ratio between responses reflected from the un-bonded areas and areas with good bond; (v) recognize a subset of the responses as being reflected from the un-bonded areas associated with the spot weld and to separate the subset from a remainder of the responses; (vi) measure the extent of the non-delamination dimensions; and (vii) present a two-dimensional color coded image of non-delamination of the spot weld (see FIG. 9). In summary, some of the distinct advantages of this invention include: (i) a three-dimensional matrix probe element; (ii) a phase delay with sub-element group to form a beam focusing and steering capability; (iii) conformable membrane (no need for an attenuation correction); and (iv) an image process utilizing electronic gates to filter out unwanted reflections.

In one exemplary embodiment, the present invention is assembled into a fully-integrated, portable (i.e., hand-held), battery-operated, non-destructive inspection system that reduces the need for destructive testing of parts and components that include welded or brazed joints. This unit includes ultrasonic phased array circuitry that is lower in cost, smaller in size, and has the capability of being battery operated, so that the device is cost effective and portable for a production line usage. Thus, the system can be used as a tool for checking the integrity of welded products with great cost-saving and efficiency. This system, which may be referred to as "EWI SpotSight™" utilizes matrix phased array (MPA) ultrasonic imaging technology to accurately assess the condition of a joint area by visualizing an ultrasonic C-scan image of the inspection area while providing real-time feedback. This system can be utilized in a wide variety of manufacturing settings for inspection of parts and components made of metals and nonmetals. The system is effective for evaluating the quality of various joining configurations including resistance spot welds, resistance seem welds, laser welds, friction stir spot welds, MIG spot welds, brazing, and others. This invention is particularly useful for: (i) the automotive industry with regard to evaluating the quality of spot welds for steel, resistance spot welds for steel and aluminum, friction stir spot welds for aluminum, and laser welds for steel; (ii) the aerospace industry with regard to evaluating the quality of resistance spot welds and resistance seam welds for aluminum, titanium, and stainless steel, and brazing for aerospace grad nickel alloys; and (iii) cleaning-in-place (CIP) applications with regard to evaluating MIG spots welds for steel, and brazing for copper and tin-coated copper.

Figure 10:
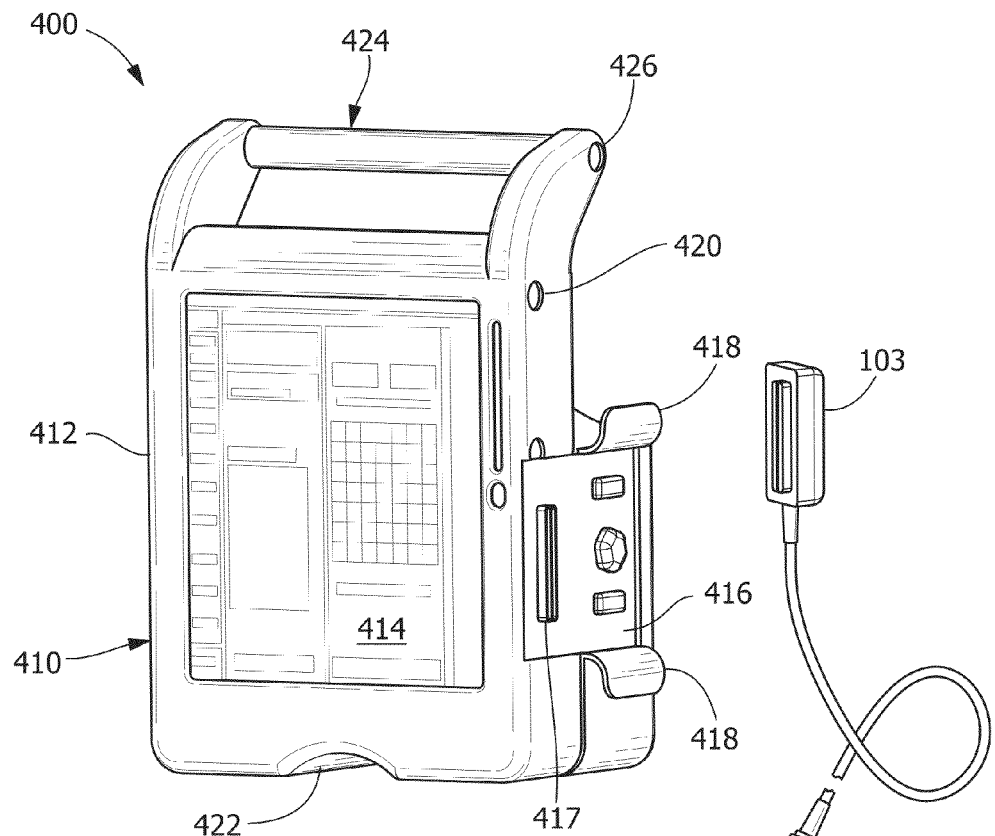
FIG. 10 is a front perspective view of a portable system for non-destructively characterizing spot welds, in accordance with an exemplary embodiment of this invention.
Figure 11:
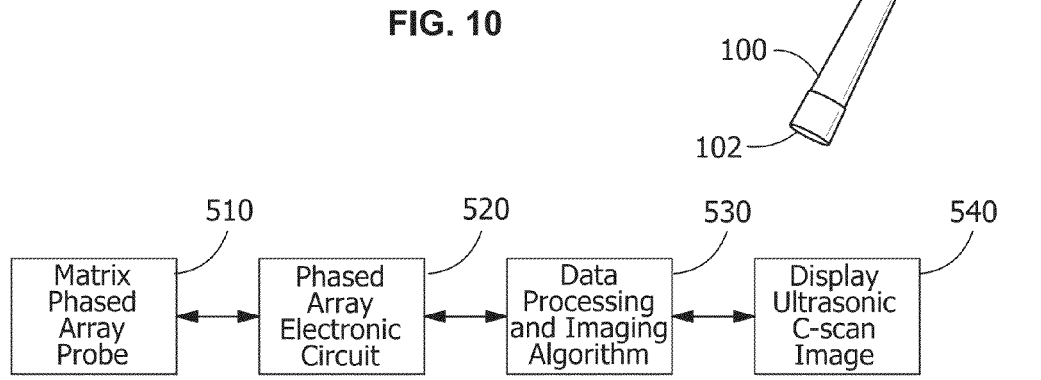
FIG. 11 is a block diagram of the basic functionality of the system of FIG. 10.

With reference to FIGS. 10-11, the portable version of this invention is intended for use as an inspection system in one or more production environments. The basic components of this system include: (i) ultrasonic phased array transmitting and receiving circuitry; (ii) a fully-integrated computer with data processing capabilities and imaging algorithm(s); (iii) at least one matrix phased array probe having a quick connect/disconnect electrical connection; and (iv) an ergonomically designed and fully portable case with a carrying handle that provides a safe storage space for the matrix phased array probe therein. As shown in FIG. 10, an exemplary embodiment of portable weld joint inspection unit 400 includes body 410 and handle 424. Body 410 further includes power switch 412, side access for USB and external monitor connections 413; screen 414, aluminum plate 416, connector adaptor 417 (e.g., Hypertronix Omni Connector adaptor); cord wrap 418, stylus storage area 420, and arm rest 422. Handle 424 further includes probe storage area 426. Probe 100 is connected to probe connector 103 (e.g., multi-pin Omni connector), which then connects to weld joint inspection unit 400 at connector adapter 417. In various exemplary embodiments, the ultrasonic phased array transmitting and receiving circuitry further includes 64-channel phased array circuitry with 16-channel simultaneous multiplexing capability; the computer includes an Intel i7 dual-core powered ruggedized tablet computer running on Windows 7 or Windows 8 operating software with a flat touch screen display that improves inspection speed by eliminating the need for a computer mouse and keyboard in a production environment; the imaging algorithm (s) further includes SpotSight™ imaging software (EWI, Inc.; Columbus, Ohio) for providing the appropriate imaging algorithm to process the data from the phased array electronics; the at least one matrix phased array probe further includes a 64-element 3-D matrix phased array probe; and the ergonomic casing further includes all features necessary for allowing cooling for the internal electronics, a handle from carrying the instrument, and various features that allow safe storage of the probe and access to all required power and data ports. Wireless connectivity (e.g., Bluetooth, Wi-Fi, cellular network, etc.) and a rechargeable battery are also typically included. The aforementioned aspects of this embodiment effectively confer the following advantageous features to the present invention, (i) the ability to quantitatively assess welds and other types of materials joining with numerical data displayed on the screen; (ii) self-contained non-destructive ultrasonic inspection system; (iii) hand-held portability; (iv) battery power; (v) touch screen and wireless functionalities; and (vi) robust quick electrical/mechanical connection of probe to the unit.

FIG. 11 provides a system block diagram that illustrates the basic functionality of an exemplary embodiment of portable weld joint inspection unit 400. In this embodiment, phased array electronic circuit 520 activates matrix phased array probe 510 with an activation command from the data processing software. Next, ultrasonic signals detected by matrix phased array probe 510 are fed to imaging algorithm 530 to be processed for fused and non-fused conditions of joining area under inspection. Finally, color coded ultrasonic C-scan image 540 is displayed on the screen with additional numerical data such as average diameter of nugget and fused area. EWI SpotSight™ processes ultrasonic signals as they are detected by the individual subgroups of the probe array using two gates, one for the front surface reflection and the other for interface reflection. An ultrasonic C-scan image is plotted as raw ultrasonic data is processed real time with the dual gate imaging algorithm. The feedback time to the operator is fraction of a second and adjustment of the probe is relatively easy and fast compared to systems for which the probe has to be repositioned if results are unsatisfactory. Despite these advantages, in examining various welds, several factors can cause undesired variations including: (i) the changing acoustic impedance of an aging membrane; (ii) natural degradation of piezoelectric elements included in the sensor/probe; (iii) slight differences between transducers; and (iv) a natural tendency of the system to undersize all welds. To compensate for these variables, some embodiments of this invention include a feature that allows the ratio between the first image gate and the second image gate to be adjusted. This feature gives an operator of the system the ability to calibrate the system to welds of known diameter, thereby increasing the overall accuracy of the system. To accomplish this, the system operator places the probe on a standard which includes a weld nugget having a known or predetermined diameter. If the image reads slightly larger or smaller than the standard, then the gate ratio is adjusted by the operator through specific inputs in the software. The image appearing on the screen of portable weld joint inspection unit 400 is created essentially by comparing the signal strength from the first gate to the strength from the second gate.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A portable system for non-destructively characterizing spot welds, comprising:
   (a) at least one matrix phased array probe, wherein the matrix phased array probe further includes:
      (i) a plurality of ultrasonic transducer elements arranged in a curved array at one end of the probe, wherein the transducer elements are operative to both generate ultrasonic signals and to receive reflections thereof; and
      (ii) a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array; and
   (b) a body, wherein the body is designed to be hand-held, and wherein the body further includes:
      (i) an ergonomically designed outer casing;
      (ii) at least one input for connecting to the at least one matrix phased array probe;
      (iii) ultrasonic phased array transmitting and receiving circuitry in electrical communication with the at least one input;
      (iv) a touch screen computer, wherein the touch screen computer further includes at least one data processor running software that includes at least one imaging algorithm for processing data received from the probe and generating color coded ultrasonic C-scan images of characterized welds; and
      (v) at least one monitor for displaying the color coded ultrasonic C-scan images of the characterized welds in real time.

2. The system of claim 1, wherein the transducer elements are further arranged into discrete subgroups, and wherein each subgroup may be activated independently of the other subgroups and at different time intervals.

3. The system of claim 2, wherein activating each subgroup independently of the other subgroups and at different time intervals for each element in the subgroup provides signal focusing and steering capability.

4. The system of claim 1, wherein the body further includes at least one rechargeable battery.

5. The system of claim 1, wherein the ergonomically designed outer casing further includes a handle, and wherein the handle has been adapted to store the matrix phased array probe.

6. The system of claim 1, wherein the ergonomically designed outer casing further includes at least one arm rest for supporting the body.

7. The system of claim 1, wherein the ultrasonic phased array transmitting and receiving circuitry further includes 64-channel phased array circuitry with 16-channel simultaneous multiplexing capability.

8. The system of claim 1, wherein the system software further include inputs that permit calibration of the system by using the matrix phased array probe to initially scan a weld joint of known diameter and then adjust system gating ratios accordingly.

9. The system of claim 1, wherein the color coded ultrasonic C-scan images further include average diameter of weld nugget and fused area for each characterized weld.

10. A portable system for non-destructively characterizing spot welds, comprising:
(a) at least one matrix phased array probe, wherein the matrix phased array probe further includes:
(i) a plurality of ultrasonic transducer elements arranged in a curved array at one end of the probe, wherein the transducer elements are operative to both generate ultrasonic signals and to receive reflections thereof; and
(ii) a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array; and
(b) a body, wherein the body is designed to be hand-held, and wherein the body further includes:
(i) an ergonomically designed outer casing, wherein the casing further includes a handle that has been adapted to store the matrix phased array probe;
(ii) at least one input for connecting to the probe;
(iii) ultrasonic phased array transmitting and receiving circuitry in electrical communication with the at least one input;
(iv) a touch screen computer, wherein the touch screen computer further includes at least one data processor running software that includes at least one imaging algorithm for processing data received from the probe and generating color coded ultrasonic C-scan images of characterized welds;
(v) at least one monitor for displaying the color coded ultrasonic C-scan images of the characterized welds in real time; and
(vi) at least one rechargeable battery.

11. The system of claim 10, wherein the transducer elements are further arranged into discrete subgroups, and wherein each subgroup may be activated independently of the other subgroups and at different time intervals.

12. The system of claim 11, wherein activating each subgroup independently of the other subgroups and at different time intervals for each element in the subgroup provides signal focusing and steering capability.

13. The system of claim 10, wherein the ergonomically designed outer casing further includes at least one arm rest for supporting the body.

14. The system of claim 10, wherein the ultrasonic phased array transmitting and receiving circuitry further includes 64-channel phased array circuitry with 16-channel simultaneous multiplexing capability.

15. The system of claim 10, wherein the system software further include inputs that permit calibration of the system by using the matrix phased array probe to initially scan a weld joint of known diameter and then adjust system gating ratios accordingly.

16. The system of claim 10, wherein the color coded ultrasonic C-scan images further include average diameter of weld nugget and fused area for each characterized weld.

17. A portable system for non-destructively characterizing spot welds, comprising:
(a) at least one matrix phased array probe, wherein the matrix phased array probe further includes:
(i) a plurality of ultrasonic transducer elements arranged in a curved array at one end of the probe, wherein the transducer elements are further arranged into discrete subgroups, wherein each subgroup may be activated independently of the other subgroups and at different time intervals; and wherein the transducer elements are operative to both generate ultrasonic signals and to receive reflections thereof; and
(ii) a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array; and
(b) a body, wherein the body is designed to be hand-held, and wherein the body further includes:
(i) an ergonomically designed outer casing, wherein the casing further includes a handle that has been adapted to store the matrix phased array probe, and at least one arm rest for supporting the body;
(ii) at least one input for connecting to the probe;
(iii) ultrasonic phased array transmitting and receiving circuitry in electrical communication with the at least one input;
(iv) a touch screen computer, wherein the touch screen computer further includes at least one data processor running software that includes at least one imaging algorithm for processing data received from the probe and generating color coded ultrasonic C-scan images of characterized welds, and wherein C-scan images further include average diameter of weld nugget and fused area for each characterized weld;
(v) at least one monitor for displaying the color coded ultrasonic C-scan images of the characterized welds in real time; and
(vi) at least one rechargeable battery.

18. The system of claim 17, wherein activating each subgroup independently of the other subgroups and at different time intervals for each element in the subgroup provides signal focusing and steering capability.

19. The system of claim 17, wherein the ultrasonic phased array transmitting and receiving circuitry further includes 64-channel phased array circuitry with 16-channel simultaneous multiplexing capability.

20. The system of claim 17, wherein the system software further include inputs that permit calibration of the system by using the matrix phased array probe to initially scan a weld joint of known diameter and then adjust system gating ratios accordingly.

* * * * *